US005466235A

United States Patent [19]

Shubin, Sr.

[11] Patent Number: 5,466,235

[45] Date of Patent: Nov. 14, 1995

[54] FEMALE FUNCTIONAL MANNEQUIN

[76] Inventor: Steven A. Shubin, Sr., 2373 Teller Rd., Suite 104, Newbury Park, Calif. 91320

[21] Appl. No.: 411,270

[22] Filed: Mar. 27, 1995

[51] Int. Cl.[6] .................... A61F 5/00

[52] U.S. Cl. .................... 600/38

[58] Field of Search .................... 600/38; 128/897–898; 434/267, 272–273

[56] References Cited

U.S. PATENT DOCUMENTS 2,763,070 9/1956 McCormick .................... 434/273

FOREIGN PATENT DOCUMENTS 2206436 1/1989 United Kingdom .................... 434/273

OTHER PUBLICATIONS

"The New Artificial Vagina" Apr. 1, 1968.

*Primary Examiner*—Angela D. Sykes
*Assistant Examiner*—John P. Lacyk
*Attorney, Agent, or Firm*—Jack C. Munro

[57] ABSTRACT

A female functional mannequin in the shape of a torso which includes an internal rigid frame upon which is mounted a muscle layer constructed of a flexible resilient material with the muscle layer essentially duplicating the form of the human female. Attached and completely enclosing the muscle layer is a flexible outer skin layer essentially duplicating human skin. A cavity is formed within the crotch of the torso. Mounted within the cavity is a cartridge which is removable. The cartridge includes an oily elastomer. Included within the oily elastomer is at least one elongated opening.

9 Claims, 5 Drawing Sheets

Fig. 5.
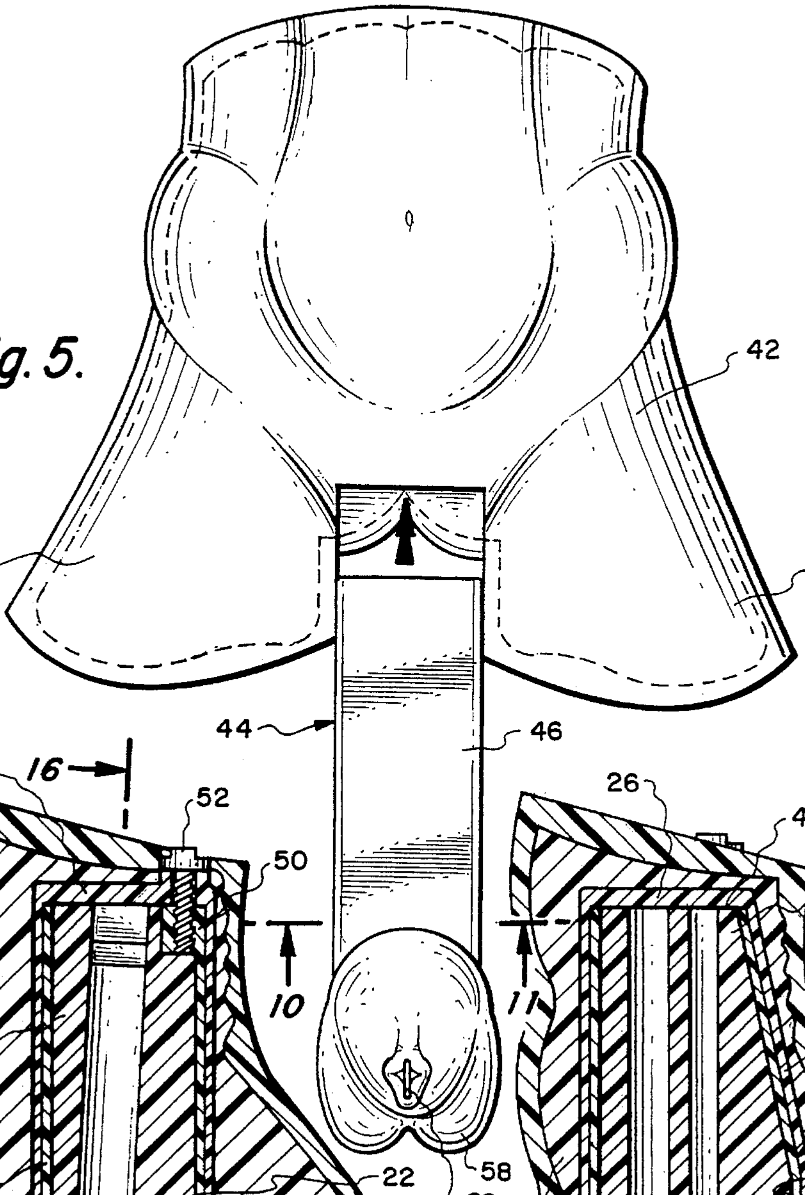
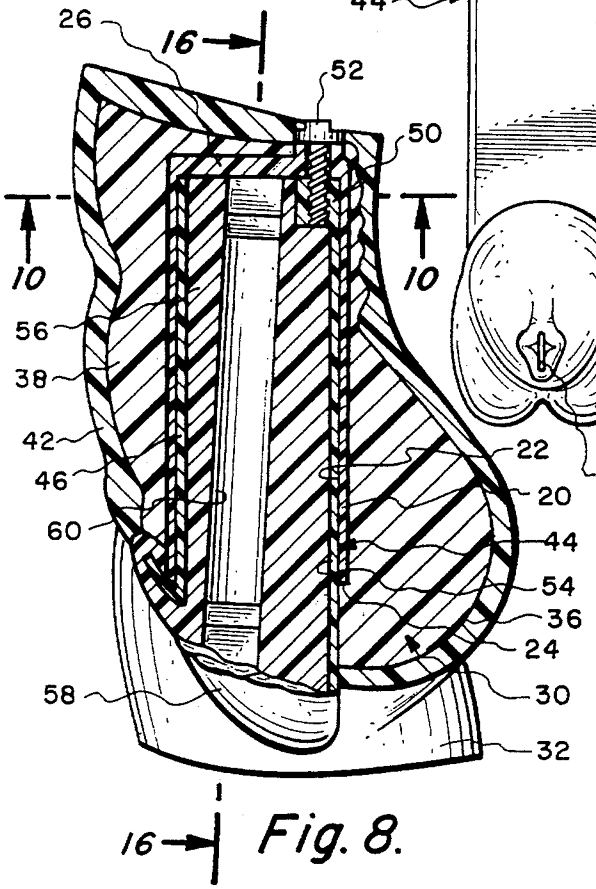
Fig. 8.
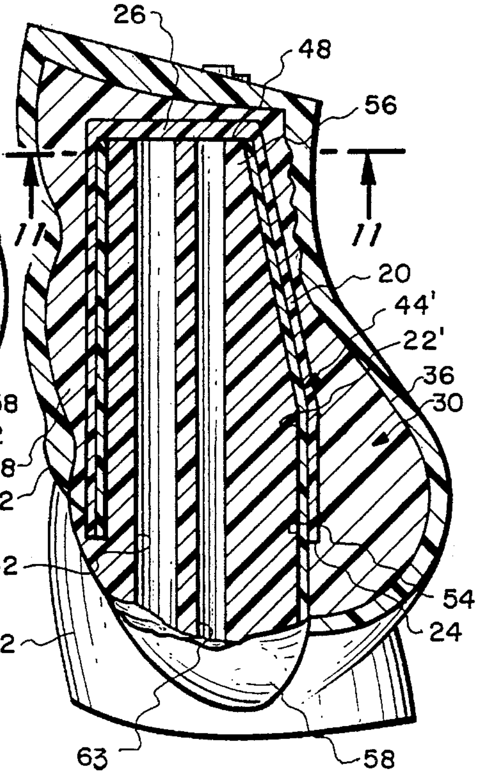
Fig. 9.

FEMALE FUNCTIONAL MANNEQUIN

BACKGROUND OF THE INVENTION

1. Field of the Invention

The field of this invention is directed to mannequins and more particularly to a mannequin that is constructed to essentially duplicate the female form.

2. Description of the Prior Art

Dolls have long been used by children. In the adult world, some individuals have been known to acquire a doll such as a inflatable doll to use as a companion. However, such dolls have incorporated minimal design characteristics and do little to essentially duplicate the form of the human female. Therefore, such dolls have not been too realistic.

There is a need to construct a realistic doll or mannequin. The realistic mannequin is to be functionally usable by the human male. Such mannequins could be used within sperm banks and also by psychiatrists in treating people with sexual disorders. Other uses for such mannequins would be to decrease the transmission of AIDS and other sexually transmitted diseases and also decrease prostitution. The use of such mannequins might also decrease the number of molestations and rapes. Such mannequins could also be used by people that are incarcerated within jails. Also, such mannequins could be used by certain individuals within the public such as individuals with certain disabilities or other individuals that, for whatever reason, do not have access to a human female.

SUMMARY OF THE INVENTION

The structure of the present invention is directed to a mannequin of the torso of the human female. The torso is constructed of a rigid frame, generally a plastic, constructed in a manner essentially duplicating the pelvic bone structure of a human female. Mounted on the frame is a flexible resilient muscle layer which totally surrounds the frame and is shaped into the form of the human female. Covering the muscle layer is a skin layer of a flexible resilient material. Located within the torso is a cavity in the area of the crotch. A cartridge is removably mounted within the crotch. The cartridge includes a rigid frame which has an interior chamber. Mounted within the interior chamber is a elastomer which is impregnated with mineral oil. The mineral oil functions to decrease friction upon an exterior Object being inserted within a through opening formed within the elastomer. A securing device is connected to the torso and functions to connect to the cartridge to secure and lock the cartridge in position when located within the cavity. The elastomer includes a plurality of spaced apart voids to provide for expansion of the elastomer upon insertion of an exterior object.

The primary objective of the present invention is to construct a female mannequin which can be sexually used by the human male with this sexual usage being not only for medical purposes but also for purposes of satisfying the sex drive of the human male.

Another objective of the present invention is to construct a female mannequin that by its usage can facilitate the collection of sperm within sperm banks as well as the collection of sperm samples for performing certain medical tests.

Another objective of the present invention is to construct a fully functional usable mannequin that can decrease the transmission of AIDS and other sexually transmitted diseases.

Another objective of the present invention is to construct a functionally female mannequin that can be used by individuals prone to molestation or rape thereby diminishing the possibility of such criminal activity.

Another objective of the present invention is to construct a functional female mannequin that can be used by individuals that have minimal or no access to a human female such as individuals with disabilities.

BRIEF DESCRIPTION OF THE DRAWINGS

FIG. 5 is a front view similar to FIG. 3 showing connection of the cartridge within the crotch of the torso of the female mannequin;

FIG. 8 is a cross sectional view through the torso taken along line 8—8 of FIG. 7 showing the position of a single longitudinal opening within the cartridge mounted within the torso;

FIG. 9 is a cross sectional view similar to FIG. 8 but showing the inclusion of a pair of longitudinal through openings within the cartridge;

DETAILED DESCRIPTION OF THE PREFERRED EMBODIMENT

Figure 1:
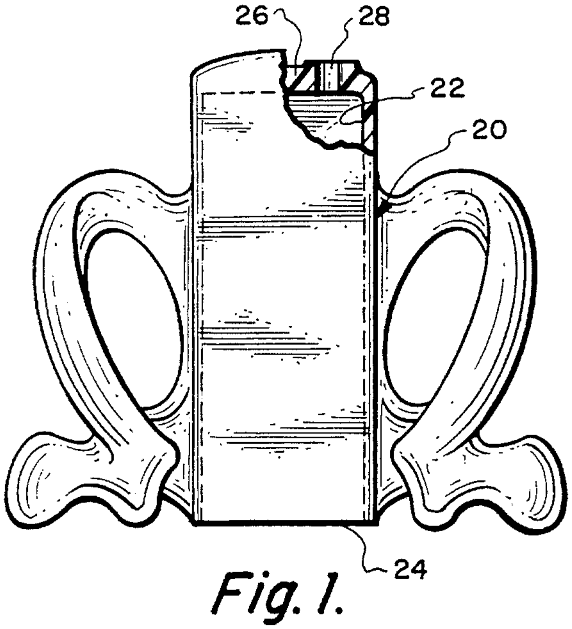
FIG. 1 is a front view of the rigid frame incorporated within the torso of the mannequin of the present invention.
Figure 2:
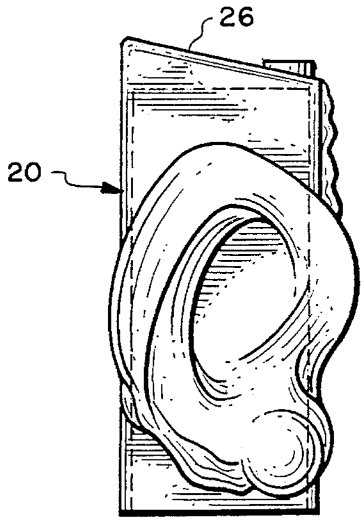
FIG. 2 is a right side view of the rigid frame shown in FIG. 1.

Referring specifically to the drawings, there is shown in FIG. 1 a rigid frame 20. The frame 20 is constructed to be basically in the shape of the pelvic bones of a human being. A typical material of construction of the frame 20 would be a plastic. The frame 20 includes an internal cavity 22 with this cavity 22 being open at front end 24. Cavity 22 is located at the crotch of the frame 20. Back end 26 of the frame 20 includes a hole 28. Attached to the frame 20, completely surrounding such, is a muscle layer 30 of material. The muscle layer 30 establishes the form of the female body. The lower end of the muscle layer 30 is formed into leg stumps 32 and 34.

Figure 7:
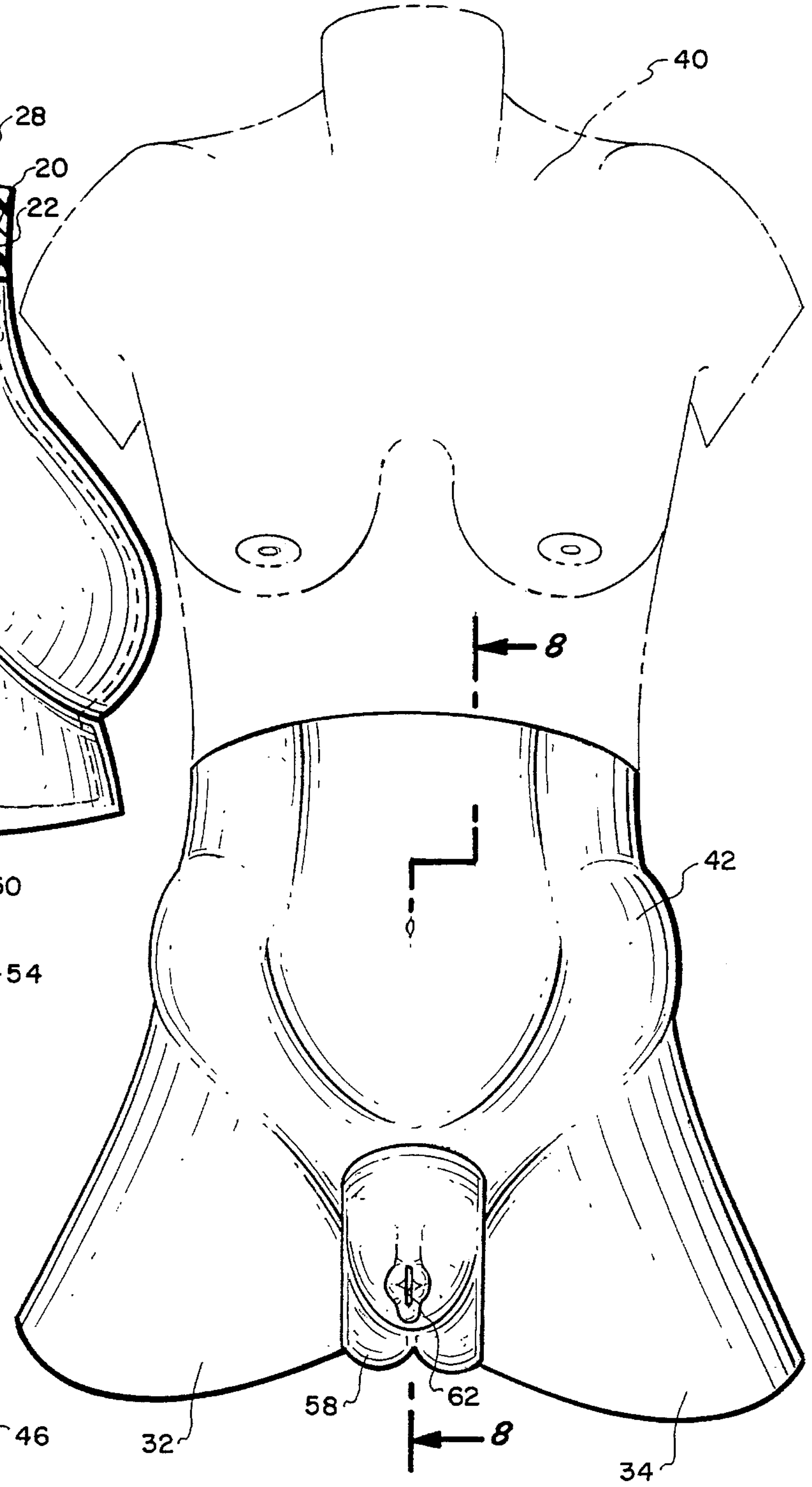
FIG. 7 is a front elevational view of a modified form of the torso which includes the addition of a chest area.
Figure 10:
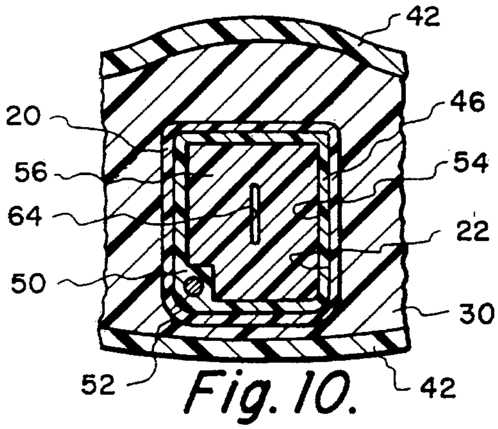
FIG. 10 is a transverse cross sectional view through the torso and cartridge taken along line 10—10 of FIG. 8.
Figure 11:
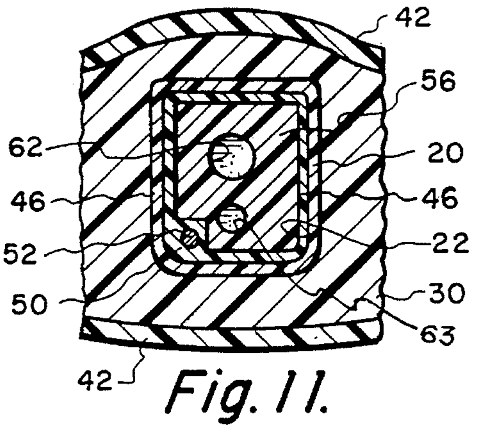
FIG. 11 is a transverse cross sectional view through the torso and cartridge taken along line 11—11 of FIG. 9.

The muscle layer 30 also defines a buttocks area 36 and a stomach area 38. Preferable material of construction for the muscle layer would be a non-skinning, polyurethane, flexible foam. This material would be cast around the frame 20. The preferable material of construction of the frame 20 would generally be a rigid, castable, urethane plastic or an injectable liquid plastic that solidifies. It is important that the material of construction for the muscle layer 30 be soft and deflectable essentially duplicating the feel that would occur if one were to manually apply pressure against a human female body. However, the muscle layer 30 is rigid enough to assume its own shape and functions to support the frame 20. It is to be understood that in referring particularly to FIG. 7 that the muscle layer 30 may be expanded to include an upper torso section 40.

Secured to the muscle layer 30 is an exterior or outer skin layer 42. The outer skin layer 42 will be cast around the muscle layer 30. Typical material for the outer skin would be a silicone or thermoplastic elastomer but also possibly a vinyl or a flexible urethane could be used. The outer skin layer 42 would normally be about one fourth of an inch thick. Hair strands could be impregnated within appropriate locations of the outer skin 42 in order to provide a realistic appearance to the human female form.

Mountable within the cavity 22 in a close fitting manner is a cartridge 44. Cartridge 44 includes a rigid outer shell 46 which generally will be constructed of a rigid plastic material. The cartridge 44 has an inner end 48 which has a threaded plug 50. The cartridge 44, when slipped within the cavity 22, is to locate the threaded plug 50 directly adjacent opening 28. A threaded fastener 52 is to connect with opening 28 and then be threadably secured within the plug 50 thereby fixing in position the cartridge 44 within the cavity 22.

The outer shell 46 of the cartridge 44 encloses an interior chamber 54. Interior chamber 54 is completely filled with an elastomer 56. Preferably, the elastomer 56 will be a thermoplastic elastomer. The actual size of the elastomer will be about eight and a half inches long, three inches in width and five inches deep. The elastomer 56 will be in the form of a gel. The elastomer includes a friction-reducing base. A desirable form of the base would be mineral oil. The gel is basically transparent, soft, flexible and has elastic memory. The gel is composed of a copolymer such as a polystyrene plastic mixed within the mineral oil. Generally, there is about at least three to four hundred percent greater amount by weight of the mineral oil than the copolymer. Although a non-petroleum oil is intended to be used, it is considered to be within the scope of this invention that a petroleum paraffinic oil could be used as well as a petroleum naphthenic oil. Also, possibly a synthetic polybutene oil could be used as well as a synthetic polypropene oil and synthetic polyterpene oil.

At the frontal surface 58 of the cartridge 44, the elastomer 56 protrudes from the rigid shell 46. This protrusion is configured to resemble the human female vulva.

Figure 16:
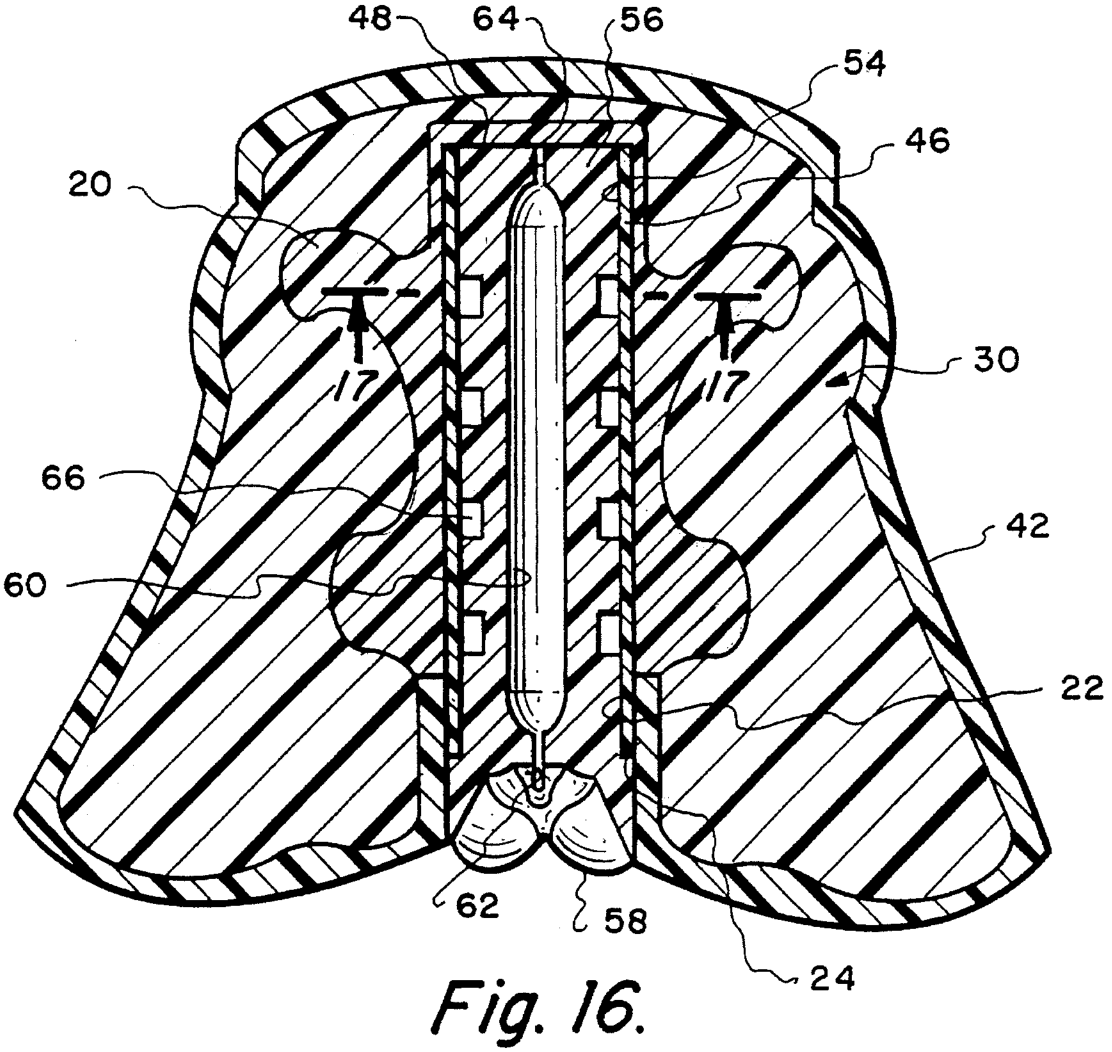
FIG. 16 is a cross sectional view through the torso and cartridge taken along line 16—16 of FIG. 8 showing the position of the voids that may be included within the elastomer located within the cartridge.
Figure 17:
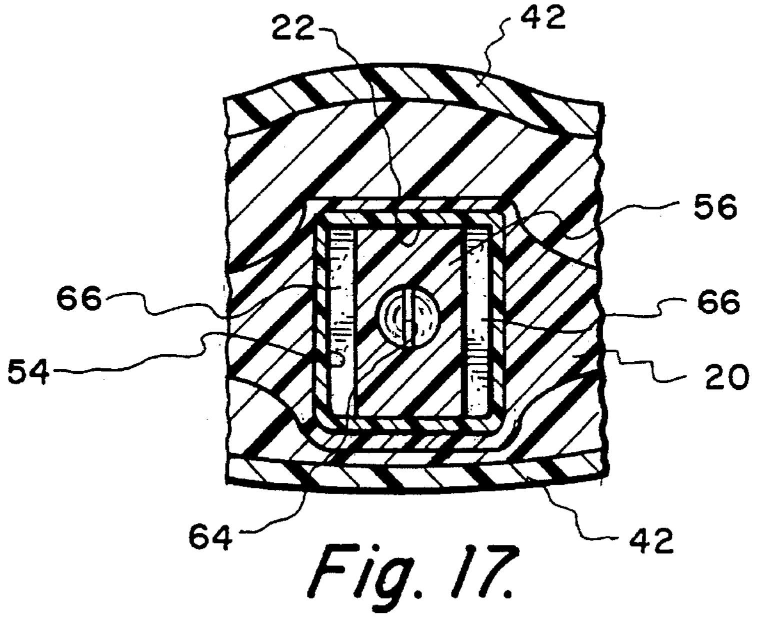
FIG. 17 is a cross sectional view taken along line 17—17 of FIG. 16.

Formed within the elastomer 56 can be either a single longitudinal opening 60, as shown in FIG. 8, or the double longitudinal openings 62 and 63, as shown in FIG. 9. The opening 60 is to be to essentially duplicate the human female vagina. The opening 63 is essentially to duplicate the human anus. The opening 60 would generally be about an inch and a half in diameter except that at each end thereof the opening 60, 62 or 63 is formed into a narrow slit such as slit 62 at the frontal surface 58 and slit 64 at the back end 48. Upon insertion of an exterior object into the opening 62, the object will be forcibly inserted through the slit 62 which will cause the slit 62 to expand. Also, there will be some expansion of the entire opening 60 with this expansion being accommodated by means of air voids 66 being formed within the elastomer 56. Referring particularly to FIG. 16, there are shown eight in number of the air voids 66. However, it is to be understood that the arrangement of the voids 66 as well as their number thereof can be varied without departing from the scope of this invention.

Any substance such as male sperm fluid that is deposited within opening 60 is to be basically retained within the opening 60 because slit 64 assumes a naturally at rest position which is substantially closed. However, when the cartridge 44 or 44' is removed from the cavity 22, a water faucet nozzle can be inserted through the slit 62 with the water then be caused to flow under high pressure through opening 60, 62 or 63. This water under pressure will cause slit 64 to be expanded and all substances contained within the appropriate opening 60, 62 or 63 be appropriately flushed from the opening.

Figure 12:
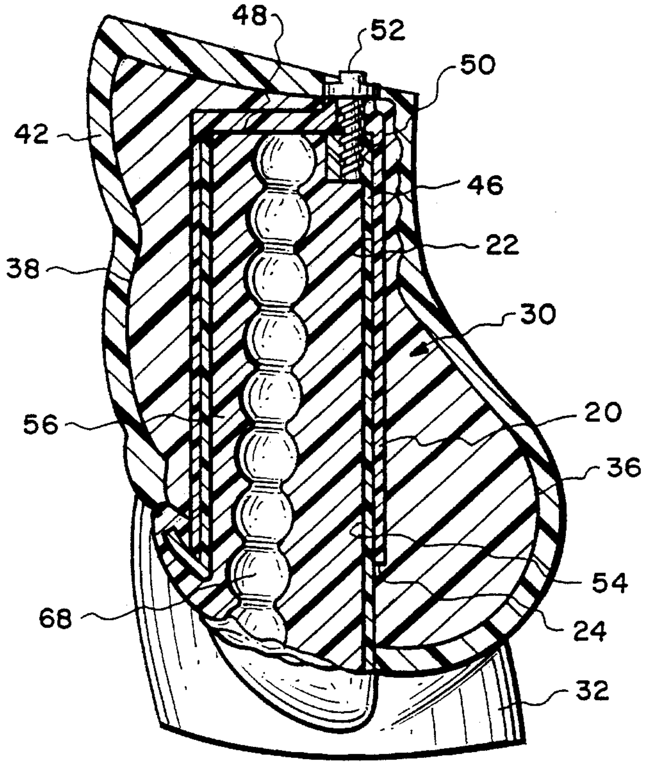
FIG. 12 is a cross sectional view similar to FIG. 8 but showing a modification of the shape of the through opening included within the cartridge.
Figure 13:
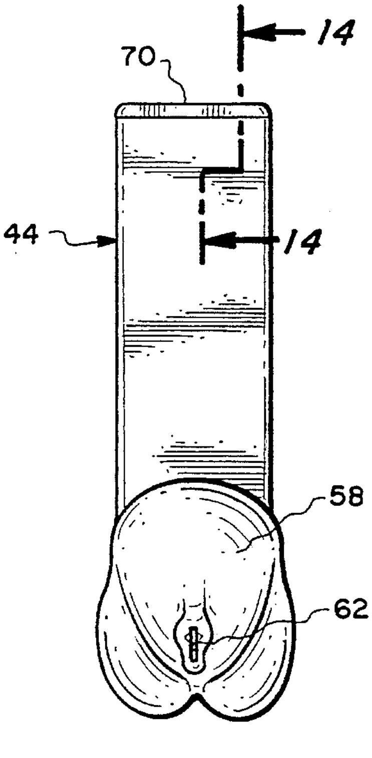
FIG. 13 is a front view of the cartridge.
Figure 14:
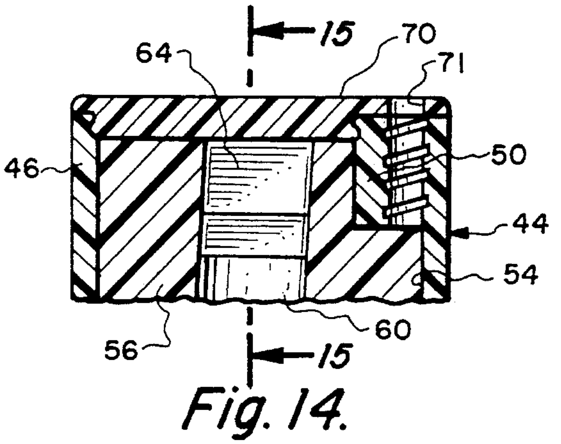
FIG. 14 is a cross sectional view through the cartridge taken along line 14—14 of FIG. 13.
Figure 15:
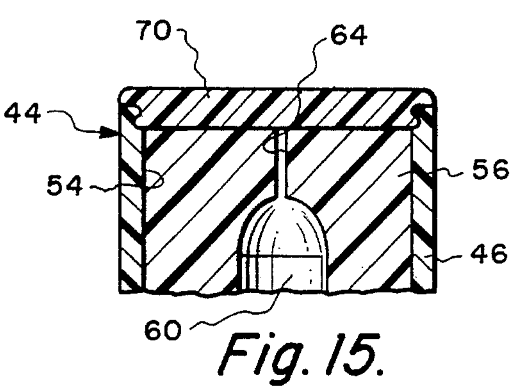
FIG. 15 is a cross sectional view taken along line 15—15 of FIG. 14.

If desired, the configuration of the opening 60 can be varied from the straight walled configuration shown in FIGS. 8, 9 and 16 to a ridged configuration as shown in opening 68 of FIG. 12. The reason for the different configuration of the walled surface of the opening 68 is so as to alter the frictional resistance upon an exterior object being placed within the opening 68.

It may be desirable to close the back end 48 of the cartridge 44. In order to do so, a cap 70 may be snapped in place at the back end 48 forming an interlocked relationship with the rigid sidewall 46 of the cartridge 44. The reason for the cap 70 is to completely close off the back end of the cartridge 44 from the cavity 22. Cap 70 would be removed when flushing the opening. The cap 70 has an opening 71 through which the threaded fastener 52 passes to connect with the threaded block 50.

In referring particularly to FIG. 9, it can be seen that the cartridge 44' is shown of a slightly different configuration than the cartridge 44. The reason for this is that because of the two openings 62 and 64 that the cartridge 44' has to be enlarged. It is to be understood that the cavity 22' is similarly enlarged.

The method of manufacture of the mannequin of the present invention is as follows: A muscle layer mold is utilized which is composed of two substantially identical halves. A release agent, which is conventional and in exceedingly common use, is sprayed or brushed onto the interior surfaces of this mold. Applied onto the release agent is then a muscle layer skin which is in liquid form and is usually applied by brush. This muscle layer skin will generally include a color. Typical material for this muscle layer skin would be product No. V-1069 entitled VI-SIL Silicone manufactured by Loctite VSI, Inc. of Troy, New York. A thin layer of this muscle layer skin is all that is required with such being generally in the range of a sixteenth to a quarter of an inch. This muscle layer skin is permitted to set which generally occurs within about ten minutes at which time this skin becomes tacky. This provides the barrier for the primary component of the muscle layer 30.

Figure 3:
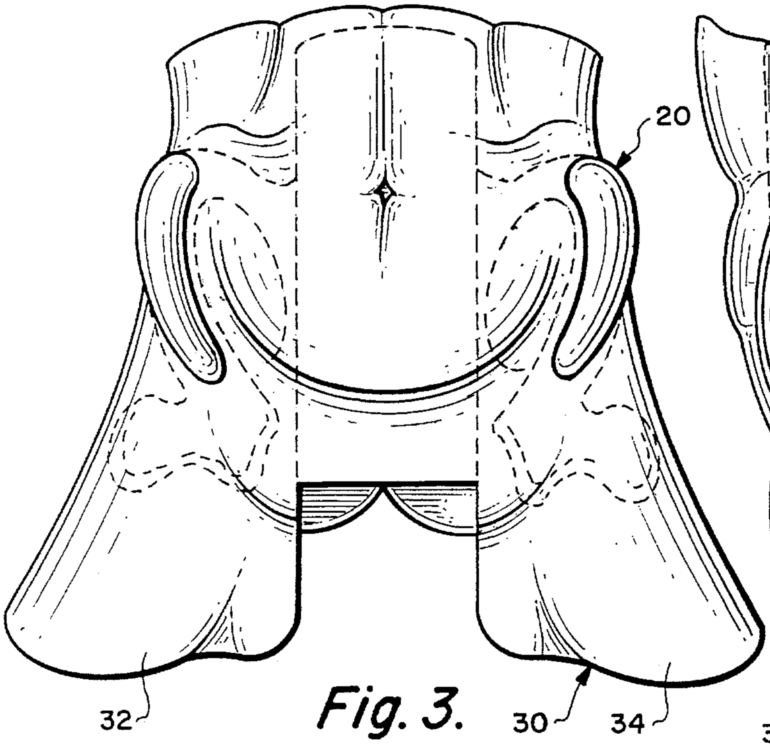
FIG. 3 is a frontal view of the torso of the mannequin of the present invention with the flexible resilient muscle layer being applied to the frame with the frame being shown in dotted lines and the flexible resilient skin being attached to the exterior surface of the muscle layer.
Figure 4:
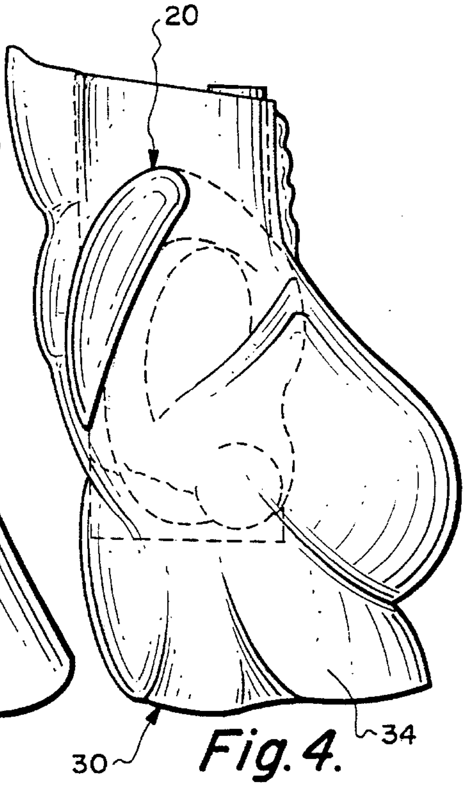
FIG. 4 is a right side view of the torso shown in FIG. 3.
Figure 6:
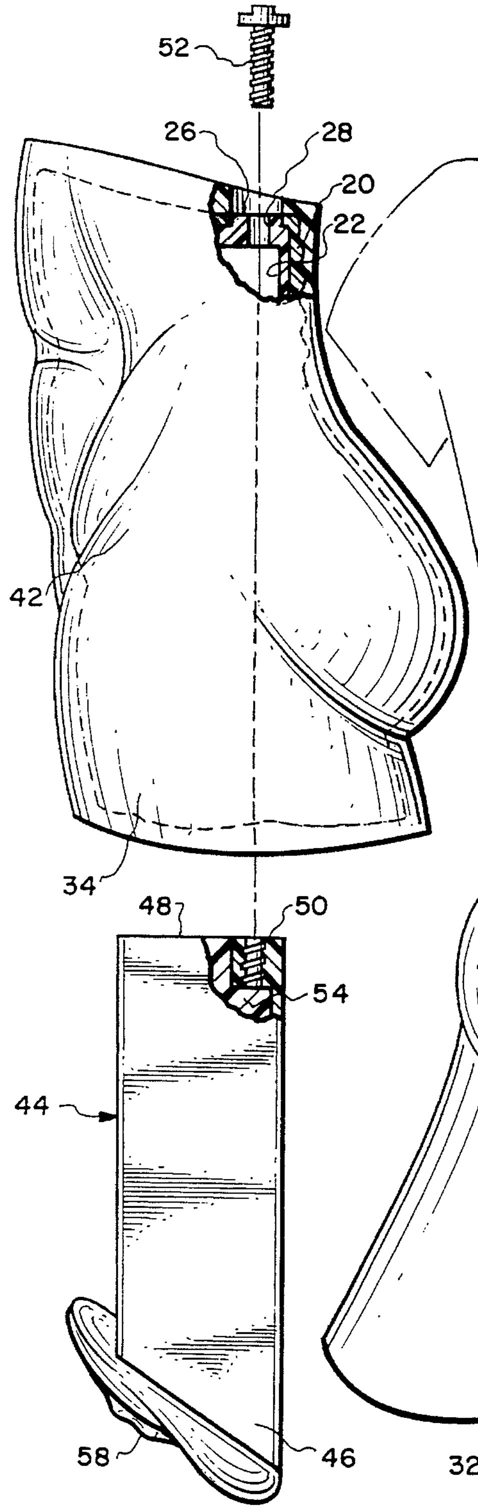
FIG. 6 is right side elevational and exploded view of the torso and cartridge showing more clearly the securing arrangement utilized between the torso and the cartridge.

The rigid frame 20 is then placed within the cavity formed by the two mold halves and precisely located in position. The two halves of the mold are then combined together enclosing the interior cavity. Within this interior cavity there is poured, in liquid form, the non-skinning polyurethane foam. Typical materials would be product No. FR 1014 manufactured by Polytech, Inc. of City of Industry, Calif. or product No. 274 from BJB Enterprises, Inc. of Garden Grove, Calif. This polyurethane foam is then permitted to set which should take about half an hour in time. The mold is then opened and the casted muscle layer 30 and frame 20 is then removed producing a part which is basically shown in FIGS. 3 and 4 of the drawings. The release agent is then to be cleaned from the muscle layer 30 by utilizing of a soft rag and a solvent such as alcohol or acetone.

The muscle layer 30 is then to be painted with an acrylic paint in an individually desirable manner. Typically, the painting would be to resemble conventional different colors of different areas of the human body. For example, the cleavage within the buttocks area would be painted a darker color than the cheeks of the buttocks area. Once this paint has dried, the paint is sealed with a silicone caulking adhesive. While this adhesive is still wet, the mannequin is then placed within an outer skin mold which is, again, composed of two separate halves which are secured together about the mannequin with the mannequin, again, being located in a precise position within the mold. When this mold is completely closed, an outer skin composition in liquid form is poured, completely filling the internal cavity of the outer skin mold. This mold is left to sit for about twenty-four hours. After that period of time, the outer skin mold is removed. There will be formed some slight seams where the crack is located between the mold halves. These seams are to be sanded down to be smoothed. The release agent that has been used in the mold is to be removed, again, by utilizing a cloth that is impregnated with a solvent such as acetone or alcohol.

The typical material of the outer skin layer 42 would be a silicone such as product No. V-1068, manufactured by Loctite VSI, Inc. of Troy, N.Y. This material comprises a pourable low viscosity rubber which is easily pigmented and is ideal for robotic and animatronic skin, special effects skin and props for theme parks and the film industry. This material is translucent. Within a typical mannequin, the muscle layer 30 will weigh about 1600 grams with the rigid frame 20 weighing about eight pounds. The rigid outer shell 46 of the cartridge 44 will weigh about six ounces. The elastomer 56 will generally weigh about three pounds.

The outer skin layer 42, in liquid form, uses about three thousand grams of product No. V-1068. Combined with this product V-1068 is a plasticizer such as an oil referred to as a DM-fluid in the amount of about fifteen hundred grams. Also added will be about three hundred grams of a catalyst which is supplied with the product No. V-1068. To this resulting composition is to be supplied a coloring agent with the typical such coloring agents being forty-seven grams of a whitecolor, thirteen grams of a light buff color, one gram of a medium blue and five grams of a sienna silicone pigment. This resulting composition will produce a weight of about forty-eight hundred and sixty-six grams which is just what is needed to produce a single mannequin. It is to be understood that more material will be used if larger sized mannequins are manufactured such as including the chest area 40.

What is claimed is:

1. A female functional mannequin comprising:

a torso having a rigid frame duplicating the pelvis of a human female, said torso having a crotch;

a muscle layer totally surrounding said rigid frame, said muscle layer comprising a flexible resilient material, said muscle layer duplicating the form of the human female;

an outer skin layer attached to said muscle layer, said outer skin layer totally covering said muscle layer, said outer skin layer comprising a flexible resilient material duplicating human skin;

a cavity formed in said crotch;

a cartridge being connected with said cavity in a snug fitting manner, said cartridge being removable, said cartridge having a rigid exterior wall surrounding an interior chamber;

a quantity of an elastomer filling said interior chamber, said elastomer having a frontal surface formed to duplicate the shape of the vulva of a human female, an opening formed within said elastomer, said opening being open at said frontal surface, said opening being longitudinally located within said cartridge, said opening forming a thin slit at said frontal surface, whereby upon an exterior object being inserted within said opening said slit expands to the cross sectional size of said exterior object.

2. The female functioning mannequin as defined in claim 1 wherein:

said muscle layer comprises a flexible polyurethane foam.

3. The female functioning mannequin as defined in claim 1 wherein:

said outer skin layer is constructed from a group consisting of silicone, thermoplastic elastomer, vinyl and flexible urethane.

4. The female functioning mannequin as defined in claim 1 wherein:

a securing means is connected to said torso, said securing means functioning to secure said cartridge within said cavity.

5. The female functioning mannequin as defined in claim 1 wherein:

said elastomer comprises a thermoplastic elastomer, said elastomer including mineral oil.

6. The female functioning mannequin as defined in claim 1 wherein:

said cartridge has a back surface, said back surface being located furthest from said frontal surface, said opening connecting with said back surface of said cartridge, a cap connecting with said back surface closing said opening, said cap being removable from said cartridge.

7. The female functioning mannequin as defined in claim 6 wherein:

said opening forms a slit at said back surface.

8. The female functioning mannequin as defined in claim 1 wherein:

said elastomer includes a plurality of spaced apart voids, whereby upon insertion of an exterior object within said opening said voids permit expansion of said elastomer decreasing the size of said voids.

9. The female functioning mannequin as defined in claim 1 wherein:

there is a second opening located within said elastomer, said second opening being located substantially parallel and spaced from said opening, said second opening being open at said frontal surface.

* * * * *